United States Patent
Sakayanagi (10) Patent No.: US 7,438,791 B2
(45) Date of Patent: Oct. 21, 2008

(54) CONCENTRATION DETECTOR

(75) Inventor: Yoshihiro Sakayanagi, Susono (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 815 days.

(21) Appl. No.: 10/899,106

(22) Filed: Jul. 27, 2004

(65) Prior Publication Data

US 2005/0077177 A1   Apr. 14, 2005

(30) Foreign Application Priority Data

Aug. 20, 2003   (JP)   ............................ 2003-208061

(51) Int. Cl.
*G01N 27/419* (2006.01)
*G01N 27/406* (2006.01)
*G01N 27/407* (2006.01)
*G01N 27/409* (2006.01)
*G01N 27/41* (2006.01)

(52) U.S. Cl. ........................ 204/425; 204/424; 204/426; 204/427; 73/23.31

(58) Field of Classification Search .......... 204/421–435
See application file for complete search history.

(56) References Cited

U.S. PATENT DOCUMENTS 6,071,393 A * 6/2000 Oshima et al. ............... 204/425
6,344,134 B1 * 2/2002 Yamada et al. ............... 205/781
6,656,337 B2 12/2003 Kurokawa et al.
2002/0130053 A1 * 9/2002 Ando et al. ................. 205/781

FOREIGN PATENT DOCUMENTS

| EP | 1 202 048 A2 | 5/2002 |
| JP | A 9-113482 | 5/1997 |
| JP | A 2000-202285 | 7/2000 |
| JP | A 2001-330586 | 11/2001 |
| JP | A 2002-202285 | 7/2002 |

* cited by examiner

*Primary Examiner*—Patrick Ryan
*Assistant Examiner*—Bach T Dinh
(74) *Attorney, Agent, or Firm*—Oliff & Berridge, PLC

(57) ABSTRACT

A concentration detector comprises oxygen-forming means for forming oxygen by decomposing the particular component in the gas, first output means for producing an output value proportional to the oxygen concentration in the gas of before oxygen is formed by the oxygen-forming means, second output means for producing an output value proportional to the oxygen concentration in the gas after oxygen is formed by the oxygen-forming means, concentration calculation means for calculating the concentration of the particular component in the gas based upon the output value from the first output means and upon the output value from the second output means by using a coefficient for bringing the output characteristics of the first output means into agreement with the output characteristics of the second output means, and means which feeds at least two kinds of gases containing the particular component at a constant concentration and containing oxygen at different concentrations to said first output means and calculates said coefficient based on the output value from the first output means and on the output value from the second output means.

7 Claims, 2 Drawing Sheets

CONCENTRATION DETECTOR

BACKGROUND OF THE INVENTION

1. Field of the Invention

The present invention relates to a concentration detector.

2. Description of the Related Art

Japanese Unexamined Patent Publication (Kokai) No. 2000-202285 discloses a device (hereinafter referred to as a "NOx detector") for detecting the concentration of nitrogen oxides (NOx) in the exhaust gas emitted from the combustion chambers of an internal combustion engine. This NOx detector includes a cell for discharging oxygen from the exhaust gas that has flowed therein (this cell in Japanese Unexamined Patent Publication (Kokai) No. 2000-202285 is designated at 110 and is called a "pump cell" and is, hence, referred to hereinafter as a "pump cell"), a cell for producing an output value corresponding to the oxygen concentration in the exhaust gas after oxygen has been discharged by the pump cell (this cell in Japanese Unexamined Patent Publication (Kokai) No. 2000-202285 is designated 120 and is called a "monitor cell" and is, hence, referred to hereinafter as a "monitor cell"), and a cell which forms oxygen by decomposing NOx in the exhaust gas after oxygen is discharged and produces an output value corresponding to the oxygen concentration in the exhaust gas after oxygen has been formed (this cell in Japanese Unexamined Patent Publication (Kokai) No. 2000-202285 is designated 130 and is called a "sensor cell" and is, hence, referred to hereinafter as a "sensor cell").

In the NOx detector disclosed in Japanese Unexamined Patent Publication (Kokai) No. 2000-202285, the pump cell discharges oxygen from the exhaust gas such that the oxygen concentration in the exhaust gas drops to a predetermined value. On the other hand, the monitor cell produces an output value (hereinafter referred to as a "monitor cell output value") corresponding to the oxygen concentration in the exhaust gas after oxygen is discharged by the pump cell. The sensor cell forms oxygen by decomposing NOx in the exhaust gas after oxygen is discharged by the pump cell and, then, produces an output value (hereinafter referred to as a "pump cell output value") corresponding to the oxygen concentration in the exhaust gas. Therefore, simply speaking, a value obtained by subtracting the monitor cell output value from the sensor cell output value will correspond to the NOx concentration in the exhaust gas. Therefore, if this value is suitably converted, then, the NOx concentration can be obtained.

As described in Japanese Unexamined Patent Publication (Kokai) No. 2000-202285 (see paragraph 0125), however, the monitor cell and the sensor cell are different in their sizes and in their constituent materials. Therefore, the output characteristics of the monitor cell are not in perfect agreement with the output characteristics of the sensor cell. Namely, a value obtained by simply subtracting the monitor cell output value from the sensor cell output value does not correspond to the NOx concentration in the exhaust gas. According to Japanese Unexamined Patent Publication (Kokai) No. 2000-202285, therefore, a coefficient (hereinafter referred to as "correction coefficient") is found for correcting the difference between the output characteristics of the monitor cell and the output characteristics of the sensor cell, the monitor cell output value is multiplied by this coefficient, the obtained value is subtracted from the sensor cell output value, and the NOx concentration in the exhaust gas is calculated based on the thus obtained value.

In the NOx detector of the above-mentioned type, the operation is necessary for bringing the output characteristics of the monitor cell into agreement with the output characteristics of the sensor cell in order to correctly calculate the NOx concentration. According to Japanese Unexamined Patent Publication (Kokai) No. 2000-202285, this operation is conducted by multiplying the monitor cell output value by the above correction coefficient that is found in advance.

Here, the output characteristics of the monitor cell and of the sensor cell vary as the NOx detector is used. Namely, as the NOx detector is continuously used, the output characteristics of the monitor cell and of the sensor cell vary due to aging of the monitor cell and the sensor cell. To correctly calculate the NOx concentration, therefore, the correction coefficient must be varied while the NOx detector is being used. If the correction coefficient that is found in advance is continuously used, then, it becomes difficult to correctly calculate the NOx concentration. This generally applies even when a particular component is calculated (detected) in the gas.

It is therefore an object of the present invention to correctly calculate the concentration of a particular component in the gas.

SUMMARY OF THE INVENTION

In order to solve the above problem according to a first invention, there is provided a concentration detector for detecting the concentration of a particular component included in a gas and forming oxygen upon being decomposed, comprising oxygen-forming means for forming oxygen by decomposing the particular component in the gas, first output means for producing an output value proportional to the oxygen concentration in the gas before oxygen is formed by the oxygen-forming means, second output means for producing an output value proportional to the oxygen concentration in the gas after oxygen is formed by the oxygen-forming means, concentration calculation means for calculating the concentration of the particular component in the gas based upon the output value from the first output means and upon the output value from the second output means by using a coefficient for bringing the output characteristics of the first output means into agreement with the output characteristics of the second output means, and means which feeds at least two kinds of gases containing the particular component at a constant concentration and containing oxygen at different concentrations to said first output means and calculates said coefficient based on the output value from the first output means and on the output value from the second output means. In the embodiment of the invention described later, the first output means corresponds to the monitor cell. In the embodiment of the invention appearing later, further, the oxygen-forming means and the second output means correspond to the sensor cell. In the embodiment of the invention appearing later, further, the particular component corresponds to NOx, ammonia or SOx.

In a second invention, as set forth in the first invention, the concentration calculation means calculates the concentration of the particular component in the gas by using a value obtained by subtracting, from the output value of the second output means, an output value of the first output means that is multiplied by said coefficient, and said coefficient is a ratio of a difference in the output values from the second output means corresponding to the oxygen concentrations in the gas in which the concentration of the particular component is zero to a difference in the output values from the first output means corresponding to the oxygen concentrations in the same gas.

In a third invention, as set forth in the second invention, if the particular component is denoted by NOx, the NOx concentration in the gas by [NOx], said coefficient by $K_3$ and two coefficients different from $K_3$ by $K_1$ and $K_2$, respectively, then, the NOx concentration calculation means calculates the concentration in the gas in compliance with the formula $[NOx]=(Is-Im\times K_3-K_2)\times K_1$, and by using the exhaust gas having a zero NOx concentration as the exhaust gas having a constant NOx concentration, there are plotted an output value of the first output means corresponding to a first oxygen concentration in the gas that has the zero NOx concentration, an output value of the second output means corresponding to the oxygen concentration in the same gas, an output value of the first output means corresponding to a second oxygen concentration in the gas having the zero NOx concentration, the second oxygen concentration being different from the first oxygen concentration and an output value of the second output means corresponding to the oxygen concentration in the same gas in a manner that the output values of the first output means are on the abscissa and the output values of the second output means are on the ordinate, and when a straight line is drawn as derived from the plotted points, the output value of the second output means at a point where the straight line intersects the ordinate represents the coefficient $K_2$.

BRIEF DESCRIPTION OF THE DRAWINGS

The present invention may be more fully understood from the description of the preferred embodiments of the invention, as set forth below, together with the accompanying drawings, in which.

DESCRIPTION OF THE PREFERRED EMBODIMENTS

Figure 1:
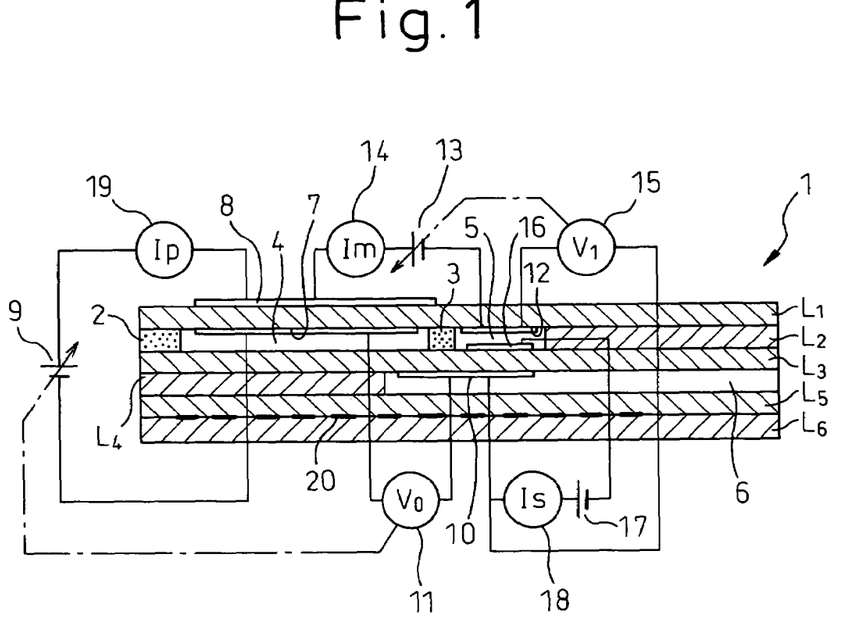
FIG. 1 is a view illustrating a sensor portion of a NOx sensor.

An embodiment of the invention will now be described with reference to the drawings. FIG. 1 illustrates the structure of a sensor portion of the NOx sensor for detecting the concentration of nitrogen oxide (NOx) in the gas. The following description deals with the NOx sensor of the embodiment which is mounted on an exhaust pipe of an internal combustion engine for detecting the NOx concentration in the exhaust gas emitted from the combustion chamber of the internal combustion engine.

Referring to FIG. 1, a sensor portion 1 of the NOx sensor comprises six electrolytic layers of an oxygen ion conducting solid material (e.g., zirconia oxide) laminated one upon the other. Hereinafter, these six solid electrolytic layers are referred to from the upper side as first layer $L_1$, second layer $L_2$, third layer $L_3$, fourth layer $L_4$, fifth layer $L_5$ and sixth layer $L_6$.

Between the first layer $L_1$ and the third layer $L_3$, there are arranged a first diffusion rate-determining member 2 and a second diffusion rate-determining member 3 made of, for example, a porous material (or fine pores have been formed). A first chamber 4 is formed between the diffusion rate-determining members 2 and 3. A second chamber 5 is formed between the second diffusion rate-determining member 2 and the second layer $L_2$. Further, an atmospheric chamber 6 communicated with the atmosphere is formed between the third layer $L_3$ and the fifth layer $L_5$. The outer side surface of the first diffusion rate-determining member 2 comes into contact with the exhaust gas. Therefore, the exhaust gas flows into the first chamber 4 through the first diffusion rate-determining member 2, and the interior of the first chamber 4 is filled with the exhaust gas.

A first cathode-side pump electrode 7 is formed on the inner peripheral surface of the first layer $L_1$ facing the first chamber 4. A first anode-side pump electrode 8 is formed on the outer peripheral surface of the first layer $L_1$. A voltage is applied across these first pump electrodes 7 and 8 from a first pump voltage source 9. When the voltage is applied across the first pump electrodes 7 and 8, oxygen contained in the exhaust gas in the first chamber 4 turns into oxygen ions upon coming in contact with the first cathode-side pump electrode 7. The oxygen ions flow toward the first anode-side pump electrode 8 through the first layer $L_1$. Therefore, oxygen contained in the exhaust gas in the first chamber 4 is pumped out migrating through the first layer $L_1$. Here, the amount of oxygen pumped out increases with an increase in the voltage of the first pump voltage source 9.

A reference electrode 10 is formed on the wall surface of the third layer $L_3$ facing the atmospheric chamber 6. Here, in the oxygen ion conducting solid electrolyte, if there is a difference in the oxygen concentration on both sides of the solid electrolytic layer, the oxygen ions migrate through the solid electrolytic layer from the side of a high oxygen concentration toward the side of a low oxygen concentration. In the example illustrated in FIG. 1, the oxygen concentration in the atmospheric chamber 6 is higher than the oxygen concentration in the first chamber 4. Upon coming in contact with the reference electrode 10, therefore, oxygen in the atmospheric chamber 6 receives electric charge and turns into oxygen ions. The oxygen ions migrate through the third layer $L_3$, second layer $L_2$ and first layer $L_1$ and carry an electric charge to the first cathode-side pump electrode 7. As a result, a voltage $V_0$ designated at 11 generates across the reference electrode 10 and the first cathode-side pump electrode 7. This voltage $V_0$ varies in proportion to the difference between the oxygen concentration in the atmospheric chamber 6 and the oxygen concentration in the first chamber 4.

In the example illustrated in FIG. 1, further, the voltage of the first pump voltage source 9 is so controlled by feedback that the voltage $V_0$ is brought into agreement with a voltage that is generated when the oxygen concentration in the first chamber 4 is 1 p.p.m. (this value is merely an example and may lie between, for example, several p.p.m. and several tens of p.p.m.). Namely, oxygen in the first chamber 4 is pumped out through the first layer $L_1$ such that the oxygen concentration in the first chamber 4 is 1 p.p.m. Thus, the oxygen concentration in the first chamber 4 is maintained at 1 p.p.m.

The first cathode-side pump electrode 7 is made of a material (e.g., an alloy of gold (Au) and platinum (Pt)) that hardly reduces NOx. Therefore, NOx contained in the exhaust gas is not almost reduced in the first chamber 4. Namely, NOx flows into the second chamber 5 passing through the second diffusion rate-determining member 3.

A second cathode-side pump electrode 12 is formed on the inner peripheral surface of the first layer $L_1$ facing the second chamber 5. A voltage is applied across the second cathode-side pump electrode 12 and the first anode-side pump electrode 8 from a second pump voltage source 13. When the voltage is applied across the pump electrodes 12 and 8, oxygen contained in the exhaust gas in the second chamber 5 turns into oxygen ions upon coming in contact with the second cathode-side pump electrode 12. The oxygen ions flow toward the first anode-side pump electrode 8 through the first layer $L_1$. Therefore, oxygen contained in the exhaust gas in the second chamber 5 is pumped out through the first layer $L_1$. Here, the amount of oxygen pumped out increases with an increase in the voltage of the second pump voltage source 13. Here, further, an electric current Im designated at 14, which is proportional to the amount of oxygen ions, flows between the second cathode-side pump electrode 12 and the first anode-side pump electrode 8.

In the oxygen ion conducting solid electrolyte, as described above, if there is a difference in the oxygen concentration on both sides of the solid electrolytic layer, the oxygen ions migrate through the solid electrolytic layer from the side of a high oxygen concentration toward the side of a low oxygen concentration. In the example illustrated in FIG. 1, the oxygen concentration in the atmospheric chamber 6 is higher than the oxygen concentration in the second chamber 5. Upon coming in contact with the reference electrode 10, therefore, oxygen in the atmospheric chamber 6 receives electric charge and turns into oxygen ions. The oxygen ions migrate through the third layer $L_3$, second layer $L_2$ and first layer $L_1$ and emit electric charge to the second cathode-side pump electrode 12. As a result, a voltage $V_1$ designated at 15 generates across the reference electrode 10 and the second cathode-side pump electrode 12. This voltage $V_1$ varies in proportion to the difference between the oxygen concentration in the atmospheric chamber 6 and the oxygen concentration in the second chamber 5.

In the example illustrated in FIG. 1, the voltage of the second pump voltage source 13 is so controlled by feedback that the voltage $V_1$ is brought into agreement with a voltage that generates when the oxygen concentration in the second chamber 5 is 0.01 p.p.m. (this value is merely an example and may assume any other value). Namely, oxygen in the second chamber 5 is pumped out through the first layer $L_1$ such that the oxygen concentration in the second chamber 5 is 0.01 p.p.m. Thus, the oxygen concentration in the second chamber 5 is maintained at 0.01 p.p.m.

The second cathode-side pump electrode 12 is made of a material (e.g., an alloy of gold (Au) and platinum (Pt)) that hardly reduces NOx. Therefore, NOx contained in the exhaust gas is not reduced even when it comes in contact with the second cathode-side pump electrode 12.

Further, a cathode-side pump electrode 16 for detecting NOx is formed on the wall surface of the third layer $L_3$ facing the second chamber 5. The cathode-side pump electrode 16 is made of a material (e.g., rhodium (Rh) or platinum (Pt)) that works to strongly reduce NOx. Therefore, NOx (in practice, NO occupying a major proportion) in the second chamber 5 is decomposed into $N_2$ and $O_2$ on the cathode-side pump electrode 16. Referring to FIG. 1, a predetermined constant voltage 17 is applied across the cathode-side pump electrode 16 and the reference electrode 10. Therefore, oxygen that is formed by decomposition on the cathode-side pump electrode 16 migrates in the form of oxygen ions toward the reference electrode 10 through the third layer $L_3$. Here, an electric current Is, designated at 18, proportional to the amount of oxygen ions flows between the cathode-side pump electrode 16 and the reference electrode 10.

Figure 2:
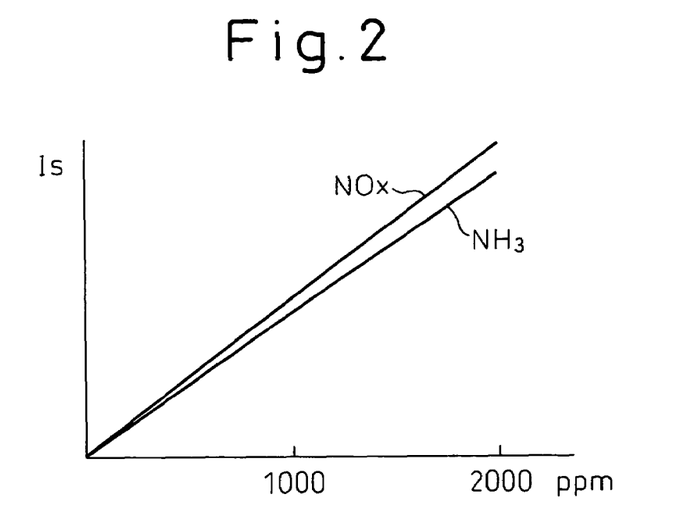
FIG. 2 is a diagram illustrating a relationship among the NOx concentration, the ammonia concentration and the electric current Is.

On the other hand, ammonia ($NH_3$) contained in the exhaust gas is decomposed into NO and $H_2O$ ($4NH_3+5O_2 \rightarrow 4NO+6H_2O$) in the first chamber 4, and the decomposed NO flows into the second chamber 5 passing through the second diffusion rate-determining member 3. The NO is decomposed into $N_2$ and $O_2$ on the cathode-side pump electrode 16, and $O_2$ that is formed by decomposition migrates as oxygen ions toward the reference electrode 10 through the third layer $L_3$. In this case, too, the current Is flows in proportion to the $NH_3$ concentration in the exhaust gas. Thus, the $NH_3$ concentration in the exhaust gas is detected from the current Is. FIG. 2 illustrates a relationship among the current Is, the NOx concentration and the $NH_3$ concentration in the exhaust gas. It will be understood from FIG. 2 that the current Is varies in proportion to the NOx concentration and the $NH_3$ concentration in the exhaust gas.

Further, as the oxygen concentration increases in the exhaust gas (i.e., as the air-fuel ratio becomes lean), oxygen is pumped out in increased amounts from the first chamber 4 and the current Ip designated at 19 increases. Therefore, the air-fuel ratio of the exhaust gas is detected from the current Ip.

A heater 20 is arranged between the fifth layer $L_5$ and the sixth layer $L_6$ for heating the sensor portion of the NOx sensor. Due to the electric heater 20, the sensor portion of the NOx sensor is heated at 700 to 800° C.

Next, described below is how to detect (calculate) the NOx concentration in the embodiment. As described above, the current Is designated at 18 assumes a value that varies in proportion to the amount of oxygen ions flowing between the cathode-side pump electrode 16 and the reference electrode 10, the oxygen ions being turned from $O_2$ formed by decomposition of NOx on the cathode-side pump electrode 16. If briefly described, therefore, the current Is assumes a value proportional to the concentration of oxygen formed by decomposition of NOx on the cathode-side pump electrode 16. In other words, the current Is varies in proportion to the NOx concentration in the second chamber 5. Therefore, the NOx concentration in the second chamber 5 (or NOx concentration in the exhaust gas) can be learned from the value of current Is.

Strictly speaking, however, oxygen ions flowing between the cathode-side pump electrode 16 and the reference electrode 10 include oxygen ions that are not pumped out from the second cathode-side pump electrode 12 migrating through the first layer $L_1$ but remain in the second chamber 5 after being formed by the cathode-side pump electrode 16 so as to flow between the cathode-side pump electrode 16 and the reference electrode 10. Accordingly, the current Is includes a current due to the amount of oxygen ions formed from NOx in the second chamber 5 and a current due to the amount of oxygen ions formed from oxygen that exists in the second chamber 5 from the first time.

Here, as described above, the current Im designated at 14 assumes a value in proportion to the amount of oxygen ions formed upon coming in contact with the second cathode-side pump electrode 12 and are flowing between the second cathode-side pump electrode 12 and the first anode-side pump electrode 8. Therefore, the current Im corresponds to a current due to the amount of oxygen ions formed from oxygen that exists in the second chamber 5 from the first time.

As described above, the current Is includes a current due to NOx in the second chamber 5 and a current due to oxygen existing in the second chamber 5 from the first time, while the current Im includes a current due to oxygen existing in the second chamber 5 from the first time. As represented by the following formula (1), therefore, a value In obtained by subtracting the current Im from the current Is will assume a value which is proportional to the NOx concentration in the second chamber 5.

$$In = Is - Im \quad (1)$$

More strictly speaking, further, if the means constituted by the cathode-side pump electrode 16 and the reference electrode 10, to produce the current Is, is called "sensor cell" and if the means constituted by the second cathode-side pump electrode and the first anode-side pump electrode 8, to produce the current Im is called "monitor cell", then, the output characteristics of the sensor cell are not often the same as the output characteristics of the monitor cell due to their sizes and the kinds of constituent materials thereof. If there is a difference in the output characteristics between the sensor cell and the monitor cell as described above, then, the value In calculated according to the above formula (1) does not vary in proportion to the NOx concentration in the exhaust gas. Besides, the sensor cell includes an output error inherent therein and the monitor cell includes an output error inherent therein. Even if these output errors are taken into consideration, it cannot be said that the value In calculated according to the above formula (1) varies in proportion to the NOx concentration in the exhaust gas.

According to this embodiment, therefore, the NOx concentration [NOx] is calculated according to the following formula (2) based upon the current Is output from the sensor cell (hereinafter also referred to as "sensor cell current") and upon the current Im output from the monitor cell (hereinafter also referred to as "monitor cell current"), $$[NOx] = (Is - Im \times K_3 - K_2) \times K_1 \quad (2)$$

where $K_3$ is a coefficient for correcting the output characteristics of the monitor cell so as to be brought into agreement with the output characteristics of the sensor cell, and $K_2$ is a coefficient for bringing the output characteristics of the monitor cell after corrected by the coefficient $k_3$ into agreement with the output characteristics of the sensor cell. That is, multiplying the monitor cell current Im by the coefficient $K_3$ is not enough for bringing the output characteristics of the monitor cell into perfect agreement with the output characteristics of the sensor cell. Therefore, the coefficient $K_2$ is used for correcting a deviation between the output characteristics of the monitor cell and the output characteristics of the sensor cell that cannot be brought into agreement with each other by using the coefficient $K_3$. Further, a coefficient $K_1$ is for converting the value $Is - Im \times K_3 - K_2$ into the NOx concentration [NOx].

Therefore, the NOx concentration in the exhaust gas can be correctly calculated (detected) according to the above formula (2) so far as the coefficients $K_1$, $K_2$ and $K_3$ assume proper values.

Here, however, it often happens that the output characteristics of the monitor cell and of the sensor cell undergo a change accompanying the deterioration of the monitor cell, and of the sensor cell as the NOx sensor is used. In this case, it is probable that the NOx concentration that is calculated may not represent a true NOx concentration even if the NOx concentration is calculated according to the above formula (2) by using the coefficient $K_3$ that is found before the monitor cell and the sensor cell are deteriorated. To correctly calculate (detect) the NOx concentration, therefore, the value of the coefficient $K_3$ must be varied (updated) depending upon changes in the output characteristics of the monitor cell and the sensor cell.

Figure 3:
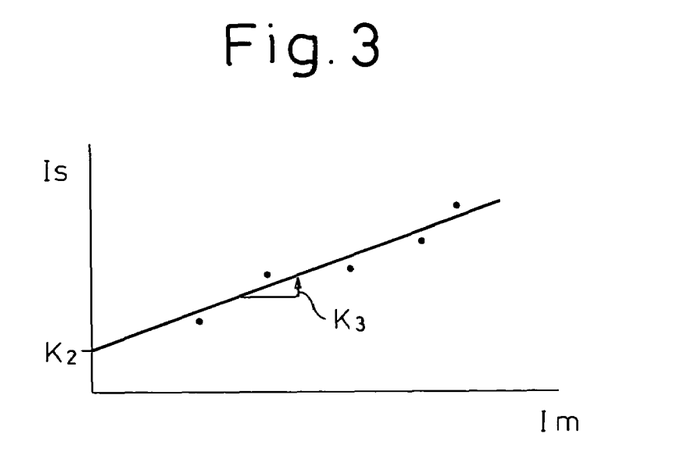
FIG. 3 is a diagram illustrating a relationship between a current Im output from a monitor cell and a current Is output from a sensor cell when the exhaust gas having the zero NOx concentration is supplied to the NOx sensor.

In this embodiment, therefore, the coefficient $K_3$ suited for correctly calculating the NOx concentration is newly calculated as described below, and the NOx concentration is calculated according to the above formula (2) by using the thus calculated coefficient $K_3$. Namely, the exhaust gas not containing NOx (i.e., exhaust gas having a zero NOx concentration) is supplied to the NOx sensor. Then, the voltage of the first pump voltage source 9 and the voltage of the second pump voltage source 13 are controlled to set various concentrations of oxygen existing in the second chamber 5 from the first time (to set at least two kinds of concentrations). The current Im and the current Is are detected for each oxygen concentration, and are plotted on the coordinates (plotting the current Im on the abscissa and plotting the current Is on the ordinate) as illustrated in FIG. 3. The plotted points are connected by a straight line (in practice, the line is not perfectly straight and is, hence, derived from the plotted points), and the gradient of the straight line is found. The gradient represents the coefficient $K_3$ which, therefore, is regarded as a new coefficient $K_3$. By using the thus found coefficient $K_3$, it is possible to correctly calculate (detect) the NOx concentration.

Next, described below is the reason why the coefficient $K_3$ thus found is used for bringing the output characteristics of the monitor cell at that moment into agreement with the output characteristics of the sensor cell at that moment. As will be understood from the foregoing, the sensor cell current Is includes a current that varies in proportion to the NOx concentration, a current that varies in proportion of the concentration of oxygen existing in the second chamber 5, and a current due to the output error inherent in the sensor cell. Therefore, if the current output from the sensor cell in proportion to the NOx concentration is denoted by "$Is_n$", the current output from the sensor cell in proportion to the concentration of oxygen existing in the second chamber 5 by "$IS_0$" and the current due to the output error inherent in the sensor cell by "$Is_{off}$", then, the sensor cell current Is is expressed by the following formula (3), $$Is = Is_n + Is_0 + Is_{off} \quad (3)$$

The monitor cell current Im, on the other hand, includes a current that varies in proportion to the concentration of oxygen existing in the second chamber 5 and a current due to the output error inherent in the monitor cell. Therefore, if the current output from the monitor cell in proportion to the concentration of oxygen existing in the second chamber 5 is denoted by "$Im_0$" and the current due to the output error inherent in the monitor cell by "$Im_{off}$", then, the monitor cell current Im is expressed by the following formula (4), $$Im = Im_0 + Im_{off} \quad (4)$$

If the above formula (2) is transformed by using these formulas (3) and (4), then, the following formula (5) is obtained, $$[NOx] = (Is_n + Is_0 + Is_{off} - (Im_0 + Im_{off}) \times K_3 - K_2) \times K_1 \quad (5)$$

The above formula can be further transformed to obtain the following formula (6), $$[NOx] = Is_n \times K_1 + (Is_0 - Im_0 \times K_3) \times K_1 + (Is_{off} - Im_{off} \times K_3 - K_2) \times K_1 \quad (6)$$

In the above formula (6), $Is_0 - Im_0 \times K_3 = 0$ must hold. Therefore, the following formula (7) is obtained. In the above formula (6), further, $Is_{off} - Im_{off} \times K_3 - K_2 = 0$ must hold. Therefore, the following formula (8) is obtained.

$$K_3 = Is_0 / Im_0 \quad (7)$$

$$K_2 = Is_{off} - Im_{off} \times K_3 \quad (8)$$

On the other hand, when the exhaust gas having a zero NOx concentration is supplied to the NOx sensor, the current $Is_n$ output from the sensor cell in proportion to the NOx concentration becomes zero since the NOx concentration is zero. Therefore, the following formula (9) is obtained from the above formula (3). Then, the current $Is_0$ output from the sensor cell in proportion to the concentration of oxygen existing in the second chamber 5 is replaced by $\alpha \times [O_2]$ ($\alpha$ is a coefficient and [$O_2$] is an oxygen concentration), and the formula (9) is transformed to obtain the formula (10), $$Is = Is_0 + Is_{off} \quad (9)$$

$$Is = \alpha \times [O_2] + Is_{off} \quad (10)$$

On the other hand, the current $Im_0$ output from the monitor cell in proportion to the concentration of oxygen existing in the second chamber 5 is replaced by $\beta \times [O_2]$ ($\beta$ is a coefficient and [$O_2$] is an oxygen concentration), and the formula (4) is transformed to obtain the formula (11), $$Im = \beta \times [O_2] + Im_{off} \quad (11)$$

Then, the above formula (10) is transformed to obtain the following formula (12), and the above formula (11) is transformed to obtain the following formula (13), $$[O_2] = (Is - Is_{off})/\alpha \quad (12)$$

$$[O_2] = (Im - Im_{off})/\beta \quad (13)$$

If the term [$O_2$] is removed by using these formulas (12) and (13), then, the following formula (14) is obtained, $$(Is - Is_{off})/\alpha = (Im - Im_{off})/\beta \quad (14)$$

The formula (14) is transformed to obtain the following formula (15), $$Is - Is_{off} = (Im - Im_{off}) \times \alpha/\beta \quad (15)$$

The formula (15) is further transformed to obtain the following formula (16), $$Is = (\alpha/\beta) \times Im + (Is_{off} - (\alpha/\beta) \times Im_{off}) \quad (16)$$

Here, $\alpha/\beta$ is replaced by "b" and $Is_{off} - (\alpha/\beta) \times Im_{off}$ is replaced by "c" to obtain the following formula (17) from the above formula (16), $$Is = b \times Im + c \quad (17)$$

Here, $K_3 = Is_0/Im_0$ as represented by the formula (7) above. If $Is_0$ is replaced by $\alpha \times [O_2]$ and $Im_0$ by $\beta \times [O_2]$, then, the coefficient $K_3$ is calculated to be $\alpha/\beta$ as given by the following formula (18), $$K_3 = \alpha \times [O_2]/(\beta \times [O_2]) = \alpha/\beta \quad (18)$$

where $\alpha/\beta$ is the coefficient b in the formula (17) above.

Further, $K_2 = Is_{off} - Im_{off} \times K_3$ as given by the formula (8) above and $K_3 = \alpha/\beta$ as given by the formula (18) above. Therefore, the coefficient $K_2$ becomes $Is_{off} - (\alpha/\beta) \times Im_{off}$ as given by the following formula (19), $$K_2 = Is_{off} - (\alpha/\beta) \times Im_{off} \quad (19)$$

Here, $Is_{off} - (\alpha/\beta) \times Im_{off}$ is the coefficient c in the above formula (17).

From the above, the formula (17) can be expressed as the following formula (20), $$Is = K_3 \times Im + K_2 \quad (20)$$

The currents Is and Im in the formula (20) are those when the exhaust gas having a zero NOx concentration is supplied to the NOx sensor. Therefore, a plurality of kinds of exhaust gases having a zero NOx concentration and different oxygen concentrations are supplied to the monitor cell to obtain currents Is and Im corresponding to these kinds of exhaust gases. These currents Is and Im are plotted on the coordinates illustrated in FIG. 3, and the plotted points are connected by a straight line. In this case, the gradient of the straight line represents the coefficient $K_3$. From the above formula (20), it will be learned that a value (intercept) of the ordinate at a point where the straight line on the coordinates meet the ordinate represents the coefficient $K_2$.

According to the method described above, not only is the coefficient $K_3$ suitably updated but also the coefficient $K_2$ is suitably updated while the NOx sensor is being used, making it possible to correctly calculate (detect) the NOx concentration at all times.

In the above-mentioned embodiment, the concentrations of oxygen existing in the second chamber 5 may be set to be two kinds of oxygen concentrations, and the coefficient $K_3$ may be a value obtained by dividing a difference in the currents Is detected by the sensor cell corresponding to the oxygen concentrations by a difference in the currents Im detected by the monitor cell corresponding to the oxygen concentrations. In other words, the concentrations of oxygen existing in the second chamber 5 may be set to be two kinds of oxygen concentrations, and the coefficient $K_3$ may be a ratio of a difference of the currents Is detected by the sensor cell corresponding to the oxygen concentrations to a difference of the currents Im detected by the monitor cell corresponding to the oxygen concentrations. If described more generally, therefore, it can be said that the invention calculates the coefficient $K_3$ based on the output (current Im) from the monitor cell and on the output (current Is) from the sensor cell of when at least two kinds of exhaust gases having the zero NOx concentration and different oxygen concentrations are supplied to the monitor cell.

Further, the above coefficient $K_3$ is calculated (updated) when it is so judged that the coefficient must be newly calculated while using the NOx sensor, when a predetermined period of time has elapsed in using the NOx sensor (when, for example, the NOx sensor is used for a predetermined period of time) or prior to using the NOx sensor.

Further, the above coefficient $K_3$ may be calculated (updated) when the exhaust gas having the zero NOx concentration has arrived at the NOx sensor (e.g., when no fuel is injected from the fuel injection valve of the internal combustion engine and, hence, when no combustion is taking place in the combustion chamber or when the air-fuel ratio in the combustion chamber is richer than the stoichiometric air-fuel ratio and no NOx is generating in the combustion chamber). In this case, there is no need to forcibly produce the exhaust gas having the zero NOx concentration and, hence, there is no need of changing the engine operating condition (e.g., there is no need of changing the amount of fuel injected from the fuel injection valve), either, offering an advantage of maintaining good engine operating condition.

In the above embodiment, the exhaust gas having the zero NOx concentration is supplied to the NOx sensor to calculate the coefficients $K_3$ and $K_2$. Namely, according to the above embodiment, the coefficient $K_3$ and the coefficient $K_2$ can be simultaneously calculated. In the following embodiment, the coefficient $K_3$ can be calculated though the coefficient $K_2$ cannot be calculated. Namely, in this embodiment, the exhaust gas having a constant NOx concentration is supplied to the NOx sensor. By controlling the voltage of the first pump voltage source 9 and the voltage of the second pump voltage source 13, the concentration of oxygen existing in the second chamber 5 is varied (to assume at least two kinds of concentrations). The current Im and the current Is are detected for each of the oxygen concentrations and are plotted on the coordinates as illustrated in FIG. 3. The plotted points are connected by a straight line (in practice, the plotted points are not connected by a perfectly straight line and, hence, the straight line is derived from the plotted points) to find the gradient of the straight line. The gradient represents the coefficient $K_3$, i.e., the new coefficient $K_3$.

Next, described below is the reason why the coefficient $K_3$ thus found is used for bringing the output characteristics of the monitor cell at that moment into agreement with the output characteristics of the sensor cell at that moment. When the exhaust gas having a constant NOx concentration is supplied to the NOx sensor, the sensor cell produces the current $Is_n$ that remains constant since the NOx concentration is constant. The current $Is_{off}$ due to the output error inherent in the sensor cell remains constant, too. In the above formula (3), therefore, if $Is_n + Is_{off}$ is replaced by "d", then, the following formula (21) is obtained, $$Is = Is_0 + d \quad (21)$$

Then, in the same manner as described above, the current $Is_0$ output from the sensor cell in proportion to the concentration of oxygen existing in the second chamber 5 is replaced by $\alpha \times [O_2]$ ($\alpha$ is a coefficient and $[O_2]$ is an oxygen concentration), and the formula (21) is transformed to obtain the following formula (22), $$Is = \alpha \times [O_2] + d \quad (22)$$

In the same manner as the above-mentioned method, further, the current $Im_0$ output from the monitor cell in proportion to the concentration of oxygen existing in the second chamber 5 is expressed by the following formula (23), $$Im = \beta \times [O_2] + Im_{off} \quad (23)$$

If the term $[O_2]$ is removed by using these formulas (22) and (23), there is obtained the following formula (24), $$Is = (\alpha/\beta) \times Im + (\alpha/\beta) \times (d - Im_{off}) \quad (24)$$

Here, since $\alpha/\beta = K_3$, the above formula (24) can be transformed into the following formula (25), $$Is = K_3 \times Im + (\alpha/\beta) \times (d - Im_{off}) \quad (25)$$

The currents Is and Im in the formula (24) are those of when the exhaust gas having a constant NOx concentration is supplied to the NOx sensor. Therefore, a plurality of kinds of exhaust gases having a constant NOx concentration and different oxygen concentrations are supplied to the monitor cell by controlling (increasing or decreasing) the voltage of the first pump voltage source 9 to obtain currents Is and Im corresponding to these kinds of exhaust gases. These currents Is and Im are plotted on the coordinates illustrated in FIG. 3, and the plotted points are connected by a straight line. In this case, the gradient of the straight line represents the coefficient $K_3$. According to the method described above, the coefficient $K_3$ is suitably updated while the NOx sensor is being used, making it possible to correctly calculate (detect) the NOx concentration at all times.

In this embodiment, too, the concentrations of oxygen existing in the second chamber 5 may be set to be two kinds of oxygen concentrations, and the coefficient $K_3$ may be a value obtained by dividing a difference in the currents Is detected by the sensor cell corresponding to the oxygen concentrations by a difference in the currents Im detected by the monitor cell corresponding to the oxygen concentrations. In other words, the concentrations of oxygen existing in the second chamber 5 may be set to be two kinds of oxygen concentrations, and the coefficient $K_3$ may be a ratio of a difference of the currents Is detected by the sensor cell corresponding to the oxygen concentrations to a difference of the currents Im detected by the monitor cell corresponding to the oxygen concentrations. Further, the above coefficient $K_3$ is calculated (updated) when it is so judged that the coefficient must be newly calculated while using the NOx sensor, when a predetermined period of time has elapsed in using the NOx sensor (when, for example, the NOx sensor is used for a predetermined period of time) or prior to using the NOx sensor.

Further, the above coefficient $K_3$ may be calculated (updated) when the exhaust gas having the constant NOx concentration has arrived at the NOx sensor (e.g., when the engine is in a steady operating condition). In this case, there is no need to forcibly produce the exhaust gas having the constant NOx concentration and, hence, there is no need to change the engine operating condition (e.g., there is no need to change the amount of fuel injected from the fuel injection valve), either, offering an advantage of maintaining good engine operating condition.

The coefficient $K_1$ can be calculated in a manner as described below. That is, a gas having a predetermined NOx concentration and having a constant oxygen concentration is supplied to the NOx sensor. In the above formula (6) in this case, the term related to the NOx concentration is $Is_n \times K_1$ only and the oxygen concentration in the gas remains constant. Therefore, the remaining term $(Is_0 - Im_0 \times K_3) \times K_1 + (Is_{off} - Im_{off} \times K_3 - K_2) \times K_1$ remains constant. Further, if the coefficients $K_2$ and $K_3$ assume suitable values, the remaining term becomes zero. After all, therefore, when the gas having the predetermined NOx concentration and the constant oxygen concentration is supplied to the NOx sensor, the above formula (6) becomes as expressed by the following formula (26), $$[NOx] = Is_n \times K_1 \quad (26)$$

The NOx concentration (i.e., [NOx] which is the left side of the formula (26)) in the gas supplied to the NOx sensor has been known, and $Is_n$ is a current Is output from the sensor cell (in practice, the current Is includes a current $Is_{off}$ due to the output error inherent in the sensor cell, and it is more correct to say that $Is_n$ can be approximated by the current Is). Therefore, the coefficient $K_1$ can be calculated from the above formula (26).

Even when it is attempted to calculate (detect) the ammonia concentration in the exhaust gas based on the sensor cell current Is, a method the same as the one described above can be utilized to correctly calculate (detect) the ammonia concentration in the exhaust gas. Further, even when it is attempted to calculate (detect) the sulfur oxide (SOx) concentration in the exhaust gas based on the sensor cell current Is, a method the same as the one described above can be utilized to correctly calculate (detect) the SOx concentration in the exhaust gas.

Though the above embodiment calculates (detects) the NOx concentration in the exhaust gas emitted from the combustion chamber of the internal combustion engine, it should be noted that the above-mentioned method can generally be applied to detecting the NOx concentration in the gas containing NOx.

Figure 4:
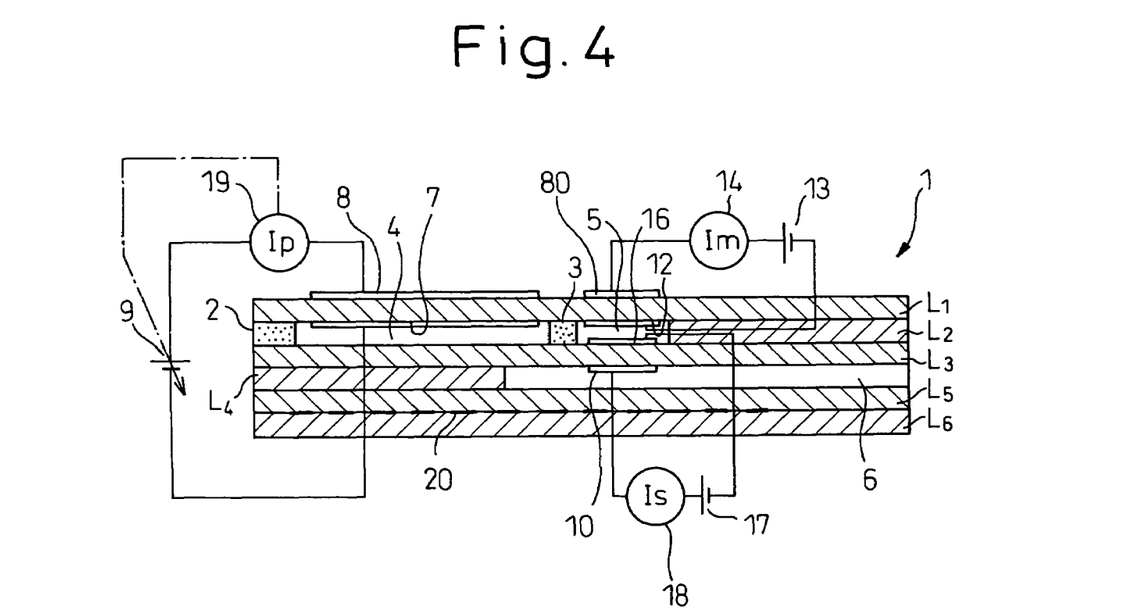
FIG. 4 is a view illustrating a sensor portion of a constitution different from that of the sensor portion illustrated in FIG. 1.

Further, the invention can be similarly applied even to the NOx sensor equipped with a sensor portion 1 illustrated in FIG. 4. That is, like the sensor portion illustrated in FIG. 1, the sensor portion 1 illustrated in FIG. 4 comprises six electrolytic layers $L_1$ to $L_6$ of an oxygen ion conducting solid material laminated one upon the other. As in the example illustrated in FIG. 1, between the first layer $L_1$ and the third layer $L_3$, there are arranged a first diffusion rate-determining member 2 and a second diffusion rate-determining member 3 to form a first chamber 4 and a second chamber 5. As in the example illustrated in FIG. 1, further, an atmospheric chamber 6 is formed between the third layer $L_3$ and the fifth layer $L_5$. As illustrated in the example of FIG. 1, further, a first cathode-side pump electrode 7 is formed on the inner peripheral surface of the first layer $L_1$, and a first anode-side pump electrode 8 is formed on the outer peripheral surface of the first layer $L_1$. A voltage is applied across these electrodes 7 and 8 from a first pump voltage source 9. When the voltage is applied across these electrodes 7 and 8 from the first pump voltage source 9, oxygen in the first chamber 4 is pumped out through the first layer $L_1$. Here, a limiting current Ip designated at 19 flows in proportion to the amount of oxygen that is pumped out. In the example illustrated in FIG. 4, the voltage of the voltage source 9 is controlled by feedback based on the limiting current Ip.

Further, a second cathode-side pump electrode 12 is formed on the inner peripheral surface of the first layer $L_1$ facing the second chamber 5, a second anode-side pump electrode 80 is formed on the outer peripheral surface of the first layer $L_1$, and a voltage is applied across these electrodes 12 and 80 from a second pump voltage source 13. When the voltage is applied across these electrodes 12 and 80 from the second pump voltage source 13, oxygen in the second chamber 5 is pumped out through the first layer $L_1$. Here, a limiting current Im designated at 14 flows in proportion to the amount of oxygen that is pumped out. Namely, the limiting current Im represents the concentration of oxygen in the second chamber 5.

Further, in the same manner as in the example of FIG. 1, an anode-side electrode 10 is formed on the wall surface of the third layer $L_3$ facing the atmospheric chamber 6, a cathode-side pump electrode 16 is formed on the wall surface of the third layer $L_3$ facing the second chamber 5, and a voltage is applied across these electrodes 10 and 16 from a voltage source 17. When the voltage is applied across these electrodes 10 and 16 from the voltage source 17, NOx is decomposed into nitrogen ($N_2$) and oxygen ($O_2$) on the cathode-side pump electrode 16, and oxygen thus formed by decomposition and oxygen existing in the second chamber 5 from the first time are pumped out to the outer side (atmospheric chamber 6) through the third layer $L_3$. Here, a limiting current Is designated at 18 flows in proportion to the amount of oxygen that is pumped out. Namely, the limiting current Is represents the total concentration of oxygen existing in the second chamber 5 from the first time and of oxygen formed by the decomposition of NOx. That is, in the example illustrated in FIG. 4, a value obtained by subtracting the limiting current Im from the limiting current Is represents the NOx concentration in the exhaust gas.

According to the present invention, even when the output characteristics of the first output means are varied or the output characteristics of the second output means are varied while the concentration detector is being used, a coefficient can be calculated every time for bringing the output characteristics of the first output means into agreement with the output characteristics of the second output means. It is therefore allowed to correctly calculate the concentration of a particular component. Further, the above coefficient may differ for each of the concentration detectors. Therefore, if it is not possible to calculate the coefficient while the concentration detector is being used, then, the coefficients must be found for each of the concentration detectors prior to using the concentration detectors. Finding the coefficients requires a cumbersome operation. However, the present invention makes it possible to calculate the coefficients while the concentration detector is being used. Therefore, the present invention also offers an advantage in that there is no need to find the coefficients for each of the concentration detectors prior to using the concentration detectors.

While the invention has been described by reference to specific embodiments chosen for purposes of illustration, it should be apparent that numerous modifications could be made thereto by those skilled in the art without departing from the basic concept and scope of the invention.

The invention claimed is:

1. A concentration detector for detecting the concentration of a particular component included in a target gas and forming oxygen upon being decomposed, comprising:
    oxygen-forming means for forming oxygen by decomposing the particular component in an inputted gas;
    first output means for producing a first output value proportional to the oxygen concentration in the inputted gas before oxygen is formed by the oxygen-forming means;
    second output means for producing a second output value proportional to the oxygen concentration in the inputted gas after oxygen is formed by the oxygen-forming means;
    concentration calculation means for calculating the concentration of the particular component in the target gas based upon the first output value and the second output value by using a coefficient for bringing the output characteristics of the first output means into agreement with the output characteristics of the second output means when inputting the target gas as the inputted gas, and
    coefficient calculation means which calculates said coefficient based on the first output values and the second output values outputted when feeding at least a first gas and a second gas as the inputted gas, respectively, the first gas containing the particular component at a predetermined constant concentration and oxygen at a first concentration, the second gas containing the particular component at the same predetermined constant concentration as the first gas and oxygen at a second concentration different from the first concentration.

2. A concentration detector as set forth in claim 1, wherein the concentration calculation means calculates the concentration of the particular component in the target gas by using a value obtained by subtracting, from the second output value, the first output value that is multiplied by said coefficient, and
    said coefficient is a ratio of a difference in the second output values outputted when feeding the first gas and the second gas as the inputted gas to a difference in the first output values outputted when feeding the first gas and the second gas to as the inputted gas in a case where the concentration of the particular component is zero.

3. A concentration detector as set forth in claim 2, wherein if the particular component is denoted by NOx, the NOx concentration in the target gas by [NOx], said coefficient by $K_3$ and two coefficients different from $K_3$ by $K_1$ and $K_2$, respectively, the concentration calculation means calculates the concentration in the target gas in compliance with the formula $[NOx]=(Is-Im \times K_3-K_2) \times K_1$, and in a case where the concentration of the NOx component is zero as the particular component, the coefficient $K_2$ is a y-intercept of a straight line determined from points plotted in a coordinate that has an abscissa (x) indicating the first output values and an ordinate (y) indicating the second output values based on the first output values and the second output values outputted when at least feeding the first gas and the second gas as the inputted gas, respectively.

4. A concentration detector as set forth in claim 1, wherein the first gas and the second gas are different from the target gas, and are produced and inputted as the inputted gas, respectively, when said coefficient is calculated.

5. A concentration detector as set forth in claim 1, wherein the coefficient calculation means calculates and updates said coefficient when a predetermined period of time has elapsed in using the concentration detector.

6. A concentration detector as set forth in claim 1, wherein the concentration calculation means adjusts the concentration of the particular component in the target gas calculated by using said coefficient, based on another coefficient that is calculated by the coefficient calculation means with said coefficient.

7. A method for detecting the concentration of a particular component included in a target gas and for forming oxygen upon being decomposed, the method comprising:

forming oxygen by decomposing the particular component in an inputted gas with a first output means having output characteristics;

producing a first output value proportional to the oxygen concentration in the inputted gas before oxygen is formed with a second output means having output characteristics;

producing a second output value proportional to the oxygen concentration in the inputted gas after oxygen is formed;

calculating the concentration of the particular component in the target gas based upon the first output value and the second output value by using a coefficient for bringing the output characteristics of the first output means into agreement with the output characteristics of the second output means when inputting the target gas as the inputted gas, and calculating said coefficient based on the first output values and the second output values outputted when feeding at least a first gas and a second gas as the inputted gas, respectively, the first gas containing the particular component at a predetermined constant concentration and oxygen at a first concentration, the second gas containing the particular component at the same predetermined constant concentration as the first gas and oxygen at a second concentration different from the first concentration.

\* \* \* \* \*